United States Patent [19]

Heyman

[11] 4,414,969

[45] Nov. 15, 1983

[54] WRIST RESTRAINT

[76] Inventor: Arnold M. Heyman, Burbank, Calif.

[21] Appl. No.: 247,270

[22] Filed: Mar. 25, 1981

[51] Int. Cl.³ ............................................. A61F 13/00
[52] U.S. Cl. ............................ 128/133; 128/DIG. 15
[58] Field of Search ........ 128/133, 134, 135, DIG. 15

[56] References Cited

U.S. PATENT DOCUMENTS

| | | | |
|---|---|---|---|
| 3,059,636 | 10/1962 | Schwartz | 128/133 |
| 3,297,026 | 1/1967 | Van Pelt | 128/133 |
| 3,535,718 | 10/1970 | Murcott | 128/133 |
| 3,535,719 | 10/1970 | Murcott | 128/133 |
| 3,857,397 | 12/1974 | Brosseau | 128/DIG. 15 |
| 3,867,930 | 2/1975 | Brown | 128/DIG. 15 |
| 3,871,381 | 3/1975 | Roslonski | 128/DIG. 15 |
| 3,903,878 | 9/1975 | Spann | 128/DIG. 15 |
| 3,939,829 | 2/1976 | Spann | 128/133 |
| 3,947,927 | 4/1976 | Rosenthal | 128/DIG. 15 |
| 4,027,666 | 6/1977 | Marx | 128/DIG. 15 |
| 4,085,746 | 4/1978 | Castiglia | 128/DIG. 15 |
| 4,237,708 | 12/1980 | Bremer, Jr. | 128/133 |

Primary Examiner—C. Fred Rosenbaum
Assistant Examiner—C. W. Shedd
Attorney, Agent, or Firm—Spensley, Horn, Jubas & Lubitz

[57] ABSTRACT

A device especially suited for restraining the movements of the limb of a patient during a medical procedure is disclosed. The device includes a generally long rectangular flexible member which encircles the limb. The outside surface of this member is a Velcro loop pile. A strap having a Velcro hook fiber surface is attached at one of its ends to the encircling member. The strap is wrapped around the encircling member in the direction toward the end closest to which the strap is attached such that the Velcro hook fiber surface of the strap is brought into contact and locking engagement with the Velcro pile surface of the encircling member. The strap is routed through a small ring attached to the outside surface of the encircling member and proceeds to a support structure to which it is releasably attached by fastening means located at or near said end. Because of the locking engagement of the Velcro surfaces of the encircling member and the strap and the small size of the ring, the encircling member cannot be substantially tightened by a pulling force exerted on or by the encircled limb in a direction away from the support structure.

12 Claims, 6 Drawing Figures

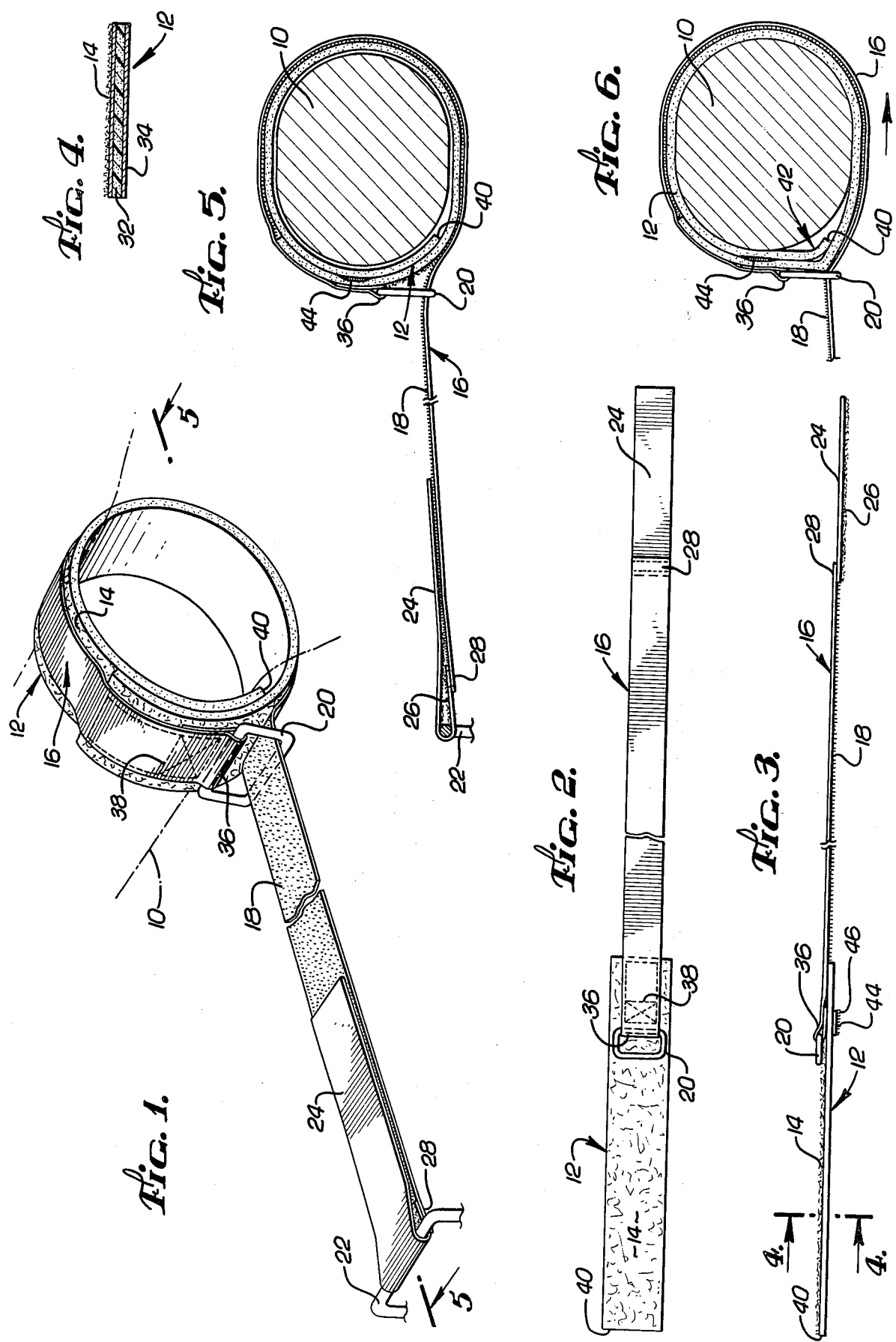

WRIST RESTRAINT

BACKGROUND OF THE INVENTION

1. Field of the Invention

This invention relates to the field of medical devices, and more particularly, to a device which can restrain the movements of a patient's limb with a minimum risk of impairing the circulation in the limb, and with the capability of being quickly removed and easily adjusted if necessary.

2. Prior Art

It is often necessary to restrain a patient's arm or leg from moving so that intravenous medication may be administered to the patient or other medical procedures performed. Typically, ropes, canvas or leather straps and buckles or other means have been used to restrain limbs from movement. It has been found that these typically used devices are not easily removable in the case of an emergency or in the event that the patient finds it necessary to be moved from the bed. In addition, many of these devices are not continuously or easily adjustable, both with regard to the tightness of the restraint about the patient's limb and with regard to the position of the restrained limb.

Under some circumstances it has been found that circulation may be impaired by devices which are either not continuously adjustable or which tighten about the patient's limb when a pulling force is exerted. Some prior art devices, however, such as the device disclosed in the Stubbs patent, U.S. Pat. No. 3,536,068, have been purposely designed to substantially tighten over a patient's limb when the patient attempts to move the limb. Such a feature, while tending to impair circulation, is intended to discourage the patient from moving and might be appropriately used for hysteria victims. However, such punitive techniques would certainly not be appropriate in all medical procedures involving rational patients and indeed could be dangerous because of the impairment of circulation which may result. In particular, an inadvertent, uncontrollable movement or shifting of position by the patient, for which no punitive measure is warranted or desirable, could still result in an undesired tightening of the restraint about the person's limb if a device such as that described by the Stubbs patent is used.

In the present device, on the other hand, there is no substantial tightening of the restraint about the patient's limb and no consequent impairment of circulation should the patient either inadvertently or purposefully move the limb. The present invention provides this feature while also providing a means for continuously adjusting both the degree of tightness of the restraint about the person's limb when it is installed and for continuously adjusting the position of the patient's limb relative to the support structure to which the restraint is attached.

In addition, the present invention provides a restraint which can be quickly released from the support structure to which it is attached in order to facilitate the handling of an emergency situation, such as where the patient must be turned to enable vomiting and to prevent aspiration.

The ability to quickly release the restraint of the present invention from the support structure to which it is attached is of great importance. Previously, restraints have been tied to a support structure. With such restraints, pulling and tugging by the patient on the restraint has, at times, so tightened the restraint to the support structure that nursing personnel have been forced to cut the restraint in order to release it. Valuable time may be lost in a futile effort to untie the restraint or in obtaining a knife or scissors with which to cut the restraint off from the support structure. This problem is completely eliminated by the quick-release feature of the present invention.

SUMMARY OF THE INVENTION

The present invention relates to a device for restraining the limbs of medical patients from movement during the administration of intravenous medication or other medical procedures. The use of the present invention can also prevent the patient from falling out of bed or dislodging other medical equipment such as nasogastric tubes, catheters, nasal cannulas, and arterial or CVP lines. The present invention can be quickly and easily attached to or removed from a patient and is continuously adjustable, both as to the member which is attached directly to the patient's limb and as to the length of the strap which attaches the device to a support structure. In addition, the present device is essentially non-punitive towards the patient, that is, it is not designed to substantially tighten about the patient's limb should the patient exert a pulling force, either inadvertently or purposefully, upon the restraining device. Such tightening may impair circulation in the patient's limb which, although perhaps temporary, might be deleterious to the medical procedure being administered and to the health of the patient.

In one form of the invention, a generally long rectangular flexible member is used in order to encircle the limb. The outside surface of this encircling member is composed of a material referred to herein as Velcro pile, i.e., it consists of tiny loops of material which are especially suitable for engaging and securely but releasably attaching to a surface composed of hook-like fibers, referred to herein as Velcro hook fibers. These Velcro materials engage upon contact and can be disengaged by a force tending to physically separate the two surfaces. Since these Velcro materials are well known, their characteristics and method of operation will not be further described.

A long securing strap, one surface of which contains Velcro hook fibers, is attached at one of its ends to the encircling member. The securing strap is wrapped around the periphery of the encircling member such that its Velcro hook fiber surface engages the Velcro pile surface of the encircling member, thus attaching the two surfaces and fixing the encircling member about the limb. The securing strap is then directed through a small ring coupled to the encircling member and towards a support structure to which it is fastened. In the preferred embodiment described herein, a short second strap having a surface containing Velcro pile is attached to the free end of the securing strap. The fastening of the device to the support structure is accomplished by the interaction of the Velcro pile surface on the second strap with the Velcro hook fiber surface located on the securing strap after a portion of this now extended strap has been looped around a support structure.

The construction of the present device is such that there will be no substantial tightening of the encircling member about the patient's limb as a result of the patient moving his or her limb and thereby tending to pull on the securing strap because of the sizing of the ring relative to the securing strap and encircling member. In the preferred embodiment to be described herein, the ring is sized so that the securing strap, when not in locking engagment with the encircling member, can be easily passed through the ring. However, where the Velcro surfaces of the securing strap and the encircling member are in locking engagement, this locked together portion of the securing strap and encircling member is too large to be easily pulled through the ring and further tightening of the device is substantially prevented. It is therefore one object of the present invention to provide a device which can comfortably restrain the limb of a medical patient without subjecting that patient's limb to the possibility of an impairment of circulation due to a tightening of the restraining device about the limb.

It is yet another object of the present invention to provide a device for restraining the movement of a patient's limb that can be quickly and easily attached or removed and can be continuously adjusted as to the snugness of the encircling member about the patient's limb and as to length of the strap used to attach the device to a support structure. With the present invention, valuable time and possibly the life of a patient will not be lost as nursing personnel attempt to untie or cut the restraint from a support structure. This result is accomplished, in the preferred embodiment, by the use of Velcro surfaces for fastening so that the restraint can be quickly released from the support structure in the event of an emergency.

It is an additional object of the present invention to provide, through the proper selection of materials, a device performing all these functions which is inexpensive, durable and machine-washable.

The novel features which are believed to be characteristic of the invention, both as to its organization and as to its method of operation, together with further objectives and advantages thereof, will be better understood from the following description considered in connection with the accompanying drawings in which a presently preferred embodiment of the invention is illustrated by way of example. It is expressly understood, however, that the drawings are for the purpose of illustration and description only, and are not intended as a definition of the limits of the invention. DR

BRIEF DESCRIPTION OF THE DRAWINGS

FIG. 1 is a perspective view of the device as it might typically be used placed in position about the wrist of a medical patient;

FIG. 2 is a plan view of the restraining device;

FIG. 3 is a side view of the restraining device;

FIG. 4 is a cross-sectional view of the encircling member of the restraining device taken in the direction of arrows 4—4 of FIG. 3;

FIG. 5 is a cross-sectional view of the restraining device taken in the direction of arrows 5—5 of FIG. 1;

FIG. 6 is a cross-sectional view of the restraining device similar to that shown in FIG. 5, illustrating that the restraining device does not substantially tighten about the limb of the patient when force is applied by the limb in the direction of the arrow.

DESCRIPTION OF THE PREFERRED EMBODIMENT

Referring first to FIG. 1, one can see the device of the present invention in its preferred embodiment as it might typically be used to restrain the limb 10 of a medical patient. As can be seen from FIG. 1, the limb 10 to be restrained is encircled by an elongated encircling member 12 the outside surface 14 of which is Velcro pile. Attached to the encircling member 12 is a long securing strap 16 which may be wrapped peripherally about the encircling member 12. That surface 18 of securing strap 16 which is placed against encircling member 12 contains Velcro hook fibers which engage the Velcro pile on the outside surface 14 of the encircling member 12. The locking engagement between the encircling member 12 and the securing strap 16 over the periphery of the encircling member 12 serves to fix the tightness of the encircling member 12 about the patient's limb 10.

After having encircled the periphery of the encircling member 12, the securing strap 16 proceeds through a small ring 20 attached at or near the surface of the encircling member 12 to a support structure 22. In the preferred embodiment, a small second strap 24, having Velcro pile surface 26 is attached to the free end 28 of the securing strap 16. The securing strap 16 and the second strap 24 may then be attached to a support structure 22 by routing them around the support structure 22 and by placing the Velcro pile surface 26 of the short second strap 24 in contact with a portion of the Velcro hook fiber surface 18 of the securing strap 16 which has not been routed around the support structure 22, thereby forming a loop around the support structure 22.

Since the Velcro hook fiber surface 18 on the securing strap 16, in the preferred embodiment, extends the entire length of the securing strap 16, the securing strap 16 may be adjusted to virtually any desired position. Furthermore, the locking engagement of the Velcro surfaces of the encircling member 12 and the securing strap 16 permits the securing strap 16 to be pulled relative to the encircled limb 10 without the occurrence of any substantial tightening of the encircling member 12 about the limb 10 of the patient.

The detailed construction of the device of the present invention can be seen with reference to FIGS. 2, 3 and 4. In the preferred embodiment, the encircling member 12 is of laminated construction, with a layer of spongy foam material 32 located between the Velcro pile surface 14 and a cloth surface 34, as shown in FIG. 4. The cloth surface 34 is fabricated from a cloth especially suitable for comfortable placement against the skin of a patient. The Velcro pile surface 14, the layer of spongy foam material 32, and the cloth layer 34 are held together by means of stitching, glue or other means. If desired, either the layer of spongy foam material 32 or the cloth layer 34 or both could be eliminated, encircling member 12 then being constructed of a single layer of material. It is also to be understood that the layer of spongy foam material 32 and the cloth layer 34 may be replaced by other suitable materials which perform the function of comfortably cushioning the encircling member 12 in its placement about the limb 10 of a patient.

A long flexible securing strap 16, one of whose surfaces 18 contains Velcro hook fibers, is attached at one of its ends to the Velcro pile surface 14 of the encircling member 12 near the end of said encircling member 12 and is oriented so that when both the encircling member 12 and the securing strap 16 are laid flat as in FIG. 2, securing strap 16 runs in a direction parallel to that of encircling member 12 with its Velcro hook surface 18 facing in a direction opposite to the direction that the Velcro pile surface 14 of encircling member 12 faces.

In the preferred embodiment at the free end 28 of securing strap 16 is attached a short flexible second strap 24 one of whose surfaces 26 is a Velcro pile material. The short second strap 24 is attached to securing strap 16 so that when both straps are laid flat as in FIG. 2, the Velcro pile surface 26 of the second strap 24 faces in the same direction as the Velcro hook fiber surface 18 of the securing strap 16.

At or near the position where the other end of securing strap 16 has been attached to encircling member 12, a small ring 20 is coupled to the encircling member 12 close to the position where the securing strap 16 is attached to the encircling member 12. In the preferred embodiment, the very end portion of securing strap 16 is passed through ring 20 and folded over upon itself, forming a small loop 36 closed over one side of ring 20. Stitching 38 is then used to hold the loop 36 closed and to attach the folded over portion of the securing strap 16 and the ring 20 to the encircling member 12, thereby also coupling ring 20 to the encircling member 12. Ring 20 is thus allowed to pivot in the loop 36 about a line or axis which is generally perpendicular to a line along the length of the device when the encircling member 12 and securing strap 16 are laid flat as shown in FIG. 2.

FIGS. 1, 5, and 6 show the device of the present invention in its preferred embodiment as it may be used to restrain the limb of a patient. Encircling member 12 is first wrapped about the limb 10 which is to be restrained starting at end 40 of the encircling member 12, the end furthest from ring 20. A pulling force then exerted on securing strap 16 serves to snugly but comfortably tighten encircling member 12 about the limb 10. Securing strap 16 is placed against the outside Velcro pile surface 14 of encircling member 12 so that its Velcro hook fiber surface 18 and the Velcro surface 14 of encircling member 12 are in continuous contact along the latter's outside periphery, thereby fixing encircling member 12 about the limb to be restrained. Securing strap 16 and the second strap 24, which is attached to the free end 28 of securing strap 16, are passed through ring 20 and routed in a direction towards support structure 22. This is done after placing the Velcro surfaces of the encircling member 12 and securing strap 16 in contact. In the preferred embodiment, attachment to a support structure 22 occurs by means on the interaction of the Velcro hook fiber surface 18 on securing strap 16 and the Velcro pile surface 26 located on the second strap 24. Securing strap 16 and the second strap 24 are passed around a portion of the support structure 22, such as is shown in FIGS. 1 and 5, and pulled to the desired degree of tightness. The Velcro pile surface 26 of the second strap 24 is then pressed against the Velcro hook fiber surface 18 of strap 16 to firmly attach the restraining device to the support structure 22.

It will be seen that the invention does not allow the encircling member 12 to be substantially tightened about the person's limb should be person either purposefully or inadvertently attempt to move the limb 10 or should the securing strap 16 otherwise be pulled upon. As can be seen in FIG. 6, some slight tightening will occur due to the pulling away from the limb 10 of the engaged encircling member 12 and the securing strap 16 in the region 42 near the ring 20 when a force, shown by the arrow in FIG. 6, is applied tending to pull the limb 10 of the patient away from the support structure 22.

The application of a more substantial force tending to pull the limb 10 of the patient away from the support structure 22 will not result in an appreciable tightening of the encircling member 12 about the limb 10 of the patient because the securing strap 16 is in locking engagement with the encircling member 12 and hence both must be pulled through ring 20 to effect such tightening. The size of ring 20 and the width and/or thickness of encircling member 12 are thus selected so that securing strap 16, when engaged with encircling member 12, cannot easily be pulled through ring 20.

In order to prevent any lateral slipping between the Velcro pile surface 14 on one side and the cloth surface 34 on the other side of the encircling member 12 in the vicinity of ring 20 opposite the stitching 38 when the patient strains and pulls upon the restraining device, a small patch of material 44 having a Velcro hook fiber surface 46 may be sewn onto the cloth surface 34 in this area, as shown in FIG. 3. The Velcro hook fiber surface 46 of this patch of material 44 engages the Velcro pile surface 14 of the encircling member 12, thereby preventing any slippage between the cloth surface 34 and the Velcro pile surface 14 of the encircling member 12.

It can be seen that the construction of the present device allows it to be quickly and easily installed, removed or adjusted. For example, if it is desired to adjust the position of the patient's limb 10, it is only necessary to apply a pulling force separating the Velcro pile surface 26 of the short second strap 24 from the Velcro hook fiber surface 18 of securing strap 16 thereby releasing the restraining device from the support structure 22. The limb 10 of the patient may then be repositioned, the straps 16 and 24 pulled to the desired degree of tightness and the Velcro pile surface 26 of the short second strap 24 placed again in contact with the Velcro hook fiber surface 18 of securing strap 16 to thereby accomplish the repositioning and resecuring of the limb 10 of the patient to the support structure 22. Similarly, any desired degree of tightness of the encircling member 12 about the limb 10 can be achieved by unfastening the device from the support structure 22, separating the Velcro surfaces 18 and 14 of the securing strap 16 and the encircling member 12, repositioning the encircling member 12, re-engaging the Velcro surfaces 18 and 14 over the periphery of the encircling member 12 and re-attaching the straps 16 and 24 to the support structure 22.

While the presently preferred embodiment has been described with respect to a specific configuration, other configurations are of course within the scope of the present invention. In other configurations, the encircling member 12 may be fabricated of other materials and still provide a snug but cushioned and comfortable fit of the encircling member 12 about the limb 10 of the patient. Alternatively, it may be desired to provide no cushioning at all or a separate external cushioning element in which case the device of the present invention would have an encircling member consisting solely of a strip of material one of whose surfaces is Velcro pile material.

Another variation of the present invention is to locate the ring 20 at a position further from the end 40 of encircling member 12 than the location at which securing strap 16 is attached to encircling member 12. Thus, in this variation, the area immediately adjacent to ring 20 on both sides is smooth. Such a configuration may enhance the ease of applying the present device in that when securing strap 16 is being passed through ring 20, the Velcro hook fiber surface 18 of strap 16, which must pass close to the Velcro pile surface 14 in order to pass through ring 20, cannot as easily accidentally engage the area adjacent to ring 20 before securing strap 16 has been pulled completely through ring 20. In this alternative configuration, the device will still essentially function in the same way as described above, as securing strap 16 remains in locking engagement with encircling member 12 over the periphery of the encircling member 12 until it reaches ring 20, except for the small area adjacent to ring 20.

Other variations of the preferred embodiment are possible by interchanging Velcro pile surfaces with the Velcro hook fiber surfaces on the various components of the present invention.

Thus, this invention is not intended to be limited to the particular embodiments specifically discussed hereinabove.

I claim:

1. A device for restraining a patient's limb or other body part comprising:

a generally rectangular, flexible encircling member of a length sufficient to encircle the limb of the patient beginning with a second end, said member having an outside surface which contains Velcro pile along substantially its entire length;

a securing strap means having a first end for peripherally holding said encircling member about said limb and having a second end for attachment to a support structure, said strap means being attached adjacent said first end to a first end of said encircling member and containing Velcro hook fibers on one surface along substantially its entire length for releasably engaging the Velcro pile located on the outside surface of said encircling member; said encircling member and securing strap means being configured and attached so that in elongated form, with said securing strap means extending beyond said first end of said encircling member, said surface of said securing strap means containing Velcro hook fibers faces in a direction opposite to that faced by the surface of said encircling member containing Velcro pile;

a ring pivotally attached to the surface of said encircling member containing Velcro pile at a position adjacent the attachment of said strap means; and a fastening means contained on said strap means for releasably attaching the second end of said securing strap means to a structure, whereby a limb is restrained by extending the encircling member and securing strap means around said limb beginning with the second end of said encircling member so that said securing strap means extends peripherally around said encircling member to hold it in place by means of the engagement of said Velcro hook fibers and said Velcro pile, and by passing the second end of said securing strap means through said ring, directing it towards a support structure and attaching said second end about the support structure using said fastening means.

2. The device of claim 1 wherein said ring is sized to prevent portions of said securing strap means and encircling member where the Velcro fibers of said securing strap means have engaged the Velcro pile of said encircling member from passing therethrough, whereby said restraining device cannot be substantially tightened about said limb by a force tending to pull said limb away from said support structure.

3. The device of claim 1 or 2 wherein said fastening means comprises a short second strap, said second strap having a surface containing Velcro pile and being attached at one end to the second end of the securing strap means so that in elongated form said second strap and said securing strap means are colinear, whereby said restraining device can be releasably attached to a support structure by passing said second strap at least partially around said support structure and by placing the surface of said short second strap containing Velcro pile in contact with a portion of the surface of said securing strap means containing Velcro hook fibers which has not been passed around said structure.

4. The device of claim 3 wherein said encircling member has cushioning means along the surface opposite to the Velcro pile surface.

5. The device of claim 3 wherein said encircling member is comprised of a thin layer of spongy foam material disposed between a surface of Velcro pile and a surface of cloth material suitable for comfortable contact with the skin.

6. The device of claim 3 wherein said encircling member contains Velcro hook fibers on its inside surface in the area opposite said ring for engaging the outside surface of said encircling member and preventing slipping between said inside and outside surfaces of said encircling member.

7. The device of claim 5 wherein a portion of said securing strap means forms a loop adjacent said first end and said ring is disposed in said loop.

8. A device for restraining the limb of a medical patient or the like comprising:

an elongated, generally flat, flexible member having a first linear portion for placement around the limb of the patient and a second linear portion attached at its first end to one end of said first linear portion, said member containing Velcro pile on one surface of the first linear portion along most of its length and Velcro hook fibers on the opposite surface of said second linear portion along most of its length, said second linear portion being circumferentially positionable to hold said first linear portion in place around the limb of the patient through the engagement of the Velcro pile on one surface of the first linear portion with the Velcro hook fibers on the opposite surface of said second linear portion and said second linear portion being attachable to a support structure;

a ring attached to that surface of said first linear portion which contains Velcro pile, said ring being attached near said first end of said second linear portion and sized so that the second end of said second linear portion can be passed therethrough; and adjustable, releasable attachment means for attaching said second linear portion of said member to a support structure.

9. A device for restraining the limb of a patient as in claim 8 wherein said adjustable, releasable attachment means is a third linear portion of said member adjacent the second end of said second linear portion, said third linear portion having Velcro pile on the same surface that said second linear portion has Velcro hook fibers, said third linear portion for looping around a support structure and adjustably attaching to said second linear portion through the engagement of said Velcro pile thereon with said Velcro hook fibers on said second linear portion.

10. A device for releasably restraining the limb of a medical patient with respect to a support structure comprising:
   an elongated cushioning member for placement circumferentially about the limb of a patient, said member having opposed first and second surfaces, said first surface for placement towards said limb and said second surface having Velcro pile along substantially the entire length of said surface;
   a ring attached to said second surface near a first end of said member;
   a first strap attached near its first end to said member near said first end of said member so that said strap is extendable colinearly with said member, said first strap for securing said cushioning member about the limb of the patient, said first strap having opposed first and second surfaces, said first surface of said first strap facing in a direction opposite to that faced by said second surface of said cushioning member when said first strap and said cushioning member are extended colinearly, said first surface of said first strap having Velcro hook fibers along substantially its entire length which engage said Velcro pile on said second surface of said cushioning member along substantially the entire periphery of said cushioning member when circumferentially placed about the limb of a patient;
   a second strap attached near its first end to the second end of said first strap so that said second strap is extendable colinearly with said first strap and said cushioning member, a first surface of said second strap facing in the direction opposite to that faced by said first surface of said first strap having Velcro hook fibers, said second end of said second strap being passable through said ring after said first strap has engaged said cushioning member along its periphery when circumferentially placed about the limb of a patient, said second strap being passable around a support structure and attachable to a portion of said first strap not passed around said support structure through the engagement of the Velcro pile on said second strap with the Velcro hook fibers on said first strap whereby said device is secured to said support structure, said ring preventing said first surface of said first strap from separating from said second surface of said cushioning member when said patient pulls their limb away from said support structure.

11. The device of claim 10 wherein said cushioning member is wider than said first strap and said second strap, and said ring has an opening whose width is less than that of said cushioning member so that said second strap and said first strap may be passed therethrough except where said first strap has engaged said cushioning member.

12. The device of claim 10 wherein said cushioning member contains Velcro hook fibers on its first surface in the area opposite said ring for engaging the second surface of said cushioning member when said cushioning member is placed circumferentially about the limb of a patient in order to prevent slipping between overlapping portions of said first and second surfaces of said cushioning member.

* * * * *